United States Patent [19]

Holmes et al.

[11] Patent Number: 4,501,792
[45] Date of Patent: Feb. 26, 1985

[54] OPERATING ROOM GOWN AND DRAPE FABRIC

[75] Inventors: Rory A. Holmes, Princeton; Eleanor Sun, East Brunswick, both of N.J.

[73] Assignee: Chicopee, New Brunswick, N.J.

[21] Appl. No.: 463,459

[22] Filed: Feb. 3, 1983

[51] Int. Cl.³ .............................................. B32B 5/06
[52] U.S. Cl. .................................... 428/299; 428/284; 428/326
[58] Field of Search ............... 428/299, 300, 301, 326, 428/221, 222, 224, 288, 284, 903; 28/103, 104

[56] References Cited

U.S. PATENT DOCUMENTS

| | | | |
|---|---|---|---|
| 3,214,819 | 11/1965 | Gueren | 428/300 |
| 3,449,809 | 6/1969 | Shin | 28/722 |
| 3,493,462 | 2/1970 | Bunting et al. | 428/300 |
| 4,041,203 | 8/1977 | Brock et al. | 428/157 |
| 4,100,324 | 7/1978 | Anderson et al. | 428/903 |
| 4,146,663 | 3/1979 | Ikeda et al. | 28/104 |
| 4,166,877 | 9/1979 | Brandon et al. | 428/221 |

FOREIGN PATENT DOCUMENTS 2074093 10/1981 United Kingdom .

Primary Examiner—James J. Bell
Attorney, Agent, or Firm—Nancy A. Bird

[57] ABSTRACT

A sterile low cost disposable fabric suitable for use in making repellant breathable drapes and gowns for use in a sterile environment, said fabric comprising rudimentary discontinuous and alternating rows of entangled cellulosic and polymeric fiber rows extending in the machine direction, and having a predominantly poylmeric surface and predominantly cellulosic surface and at least said cellulosic fibers being subject to a repellant treatment, yielding a breathable repellant soft fabric with enhanced drape and enhanced frictional properties.

4 Claims, 8 Drawing Figures

FIG-1 *PRIOR ART*
FIG-2

FIG-7  *PRIOR ART*
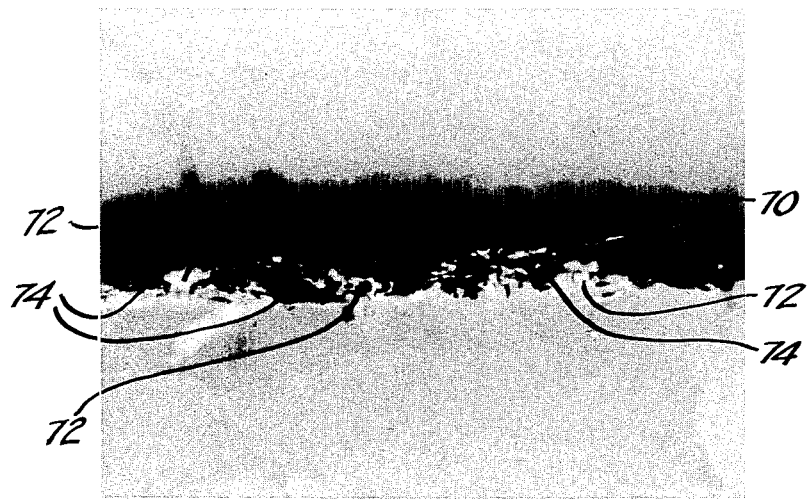
FIG-8
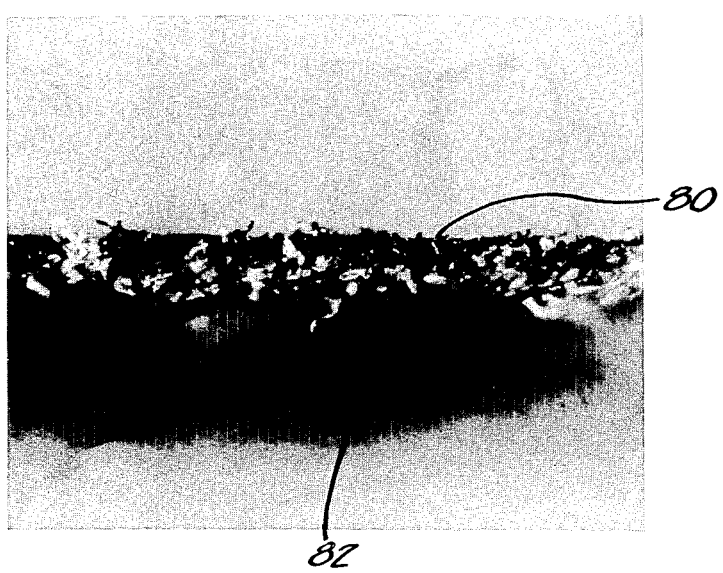

OPERATING ROOM GOWN AND DRAPE FABRIC

BACKGROUND OF THE INVENTION

The prior art contains many examples of fabrics developed for use in disposable hospital gowns, surgical drapes, and wraps for medical components. These fabrics, which must be fluid repellant and themselves sterilizable, are used to maintain sterility by providing a barrier to contamination. In the case of fabrics used for making gowns the fabric needs also to be breathable and possess sufficient drape for comfort. U.S. Pat. No. 4,041,203 discloses a fabric developed for use as a wrap, gown or surgical drape. The fabric is a laminar structure having a top layer comprising a mat of discontinuous thermoplastic microfibers and the bottom layer comprising a web of thermoplastic continuous fibers, which layers are then bonded in discrete intermittent regions using, for example, heat to laminate the two layers together. UK Patent Application No. 2,074,093 discloses another laminar fabric suitable for use in hospital gowns or tents. The laminar structure comprises a flexible layer of hydrophobic material and a continuous hydrophilic layer. As described in the application, the layers may be fastened together by sewing or by an adhesive, or the hydrophilic layer may be cast directly onto the microporous hydrophobic layer, and sufficient hydraulic force applied to force the hydrophilic polymer to penetrate into the surface void spaces of the hydrophobic layer.

The prior art also contains many disclosures of entangled fiber fabrics; nonwoven fabrics formed by hydraulic entangling. U.S. Pat. No. 3,493,462 discloses a nonpatterned fabric of interentangled fibrous material selected from the group consisting of cellulosic and synthetic textile fibers. U.S. Pat. No. 3,214,819 discloses various methods of producing entangled fiber fabrics including nonpatterned fabrics, or fabrics with a core or fabrics with a backing. U.S. Pat. No. 4,146,663 discloses a composite fabric formed by entangling extremely fine individual fibers having a average diameter of 0.1 to 6.0 microns into a woven or knitted fabric, said fabric being disclosed as a substratum for artificial leather.

U.S. Pat. No. 3,449,809 discloses an improved process for producing nonwovens with the entangling method by using a polymeric additive in the water. This patent discloses that the improved process may also be used to stitch an assemblage together by entangling fibers from a top layer into and through lower layers. Defensive publication 17060 discloses a two-sided laminar fabric formed by uniting a web of synthetic fibers with paper sheet by mechanical entangling, fluid entanglement and/or bonding. Applicants' fabric is a two-sided fabric, but comprises alternating entangled discontinuous rows of polymeric fibers and wood pulp fibers. The publication contains no disclosures of entangled rows of polymeric fibers and wood pulp fibers. A duPont fabric sold under the name Fabric 450 TM comprises an entangled fabric of polymeric and wood pulp fibers containing alternating rows of wood pulp and polymeric fibers with a thin veneer of wood pulp on one surface thereof.

SUMMARY OF THE INVENTION

The present invention comprises a sterile low-cost disposable fabric suitable for making repellant breathable surgical drapes, wraps for medical components, and gowns with enhanced comfort for hospital use or use within a sterile environment. The fabric has enhanced softness and drape and enhanced frictional properties. The fabric consists of entangled cellulosic fibers and entangled polymeric fibers. The fabric has a predominantly cellulosic fiber face and a predominantly polymeric fiber face. The polymeric fibers and cellulosic fibers are each entangled into rudimentary discontinuous and alternating rows extending in the machine direction of the fabric. At least the cellulosic fibers are subject to a repellant treatment. The cellulosic fibers present at the surface of the predominantly polymeric fiber surface are present in an overall nonpatterned distribution. The fabric is breathable, repellant and soft. The enhanced drape of the fabric makes it easier to handle and fold as a wrap for medical components. When used as a surgical drape, the fabric more easily conforms to uneven surface and more easily falls away from the upper surface of, for instance, a table or mayo stand effectively getting the fabric out of the way of the operating room personnel. The enhanced frictional properties of the fabric lend to its characteristics as a wrap for medical components in that the wrap is not easily dislodged and does not easily come unwrapped. When used as a surgical drape, the enhanced frictional properties provide a drape which will more easily stay where it is initially placed and may provide a nonslip, gripping surface for surgical instruments and the like disposed on the drape. The enhanced softness and drape of the fabric provide a gown or other wearing apparel with improved comfort to the wearer.

BRIEF DESCRIPTION OF THE DRAWINGS

FIG. 1 is a 20× photomacrograph of a plan view of the "polymeric fiber surface" of a prior art fabric.

FIG. 2 is a 20× photomacrograph of a plan view of the polymeric surface of the fabric according to the present invention.

FIG. 7 is a 35× photomacrograph giving a cross-section of the prior art fabric of FIG. 1.

FIG. 8 is a 35× photomacrograph giving a cross-section of a fabric according to the present invention.

DETAILED DESCRIPTION OF THE DRAWINGS

FIGS. 1 and 2 show a prior art fabric, Fabric 450 TM and the fabric according to the present invention. Both fabrics are made with polyester and wood pulp. Both fabrics have a predominantly wood pulp fiber surface which is not shown. Applicants' fabric is a two-sided fabric with a wood pulp surface and a polymeric fiber surface. The polymeric fiber surface of Applicants' fabric is shown in FIG. 2. FIG. 1 shows the other surface of the prior art fabric which is designated "polymeric fiber surface" for easy comparison with Applicants' polymeric fiber surface. The wood pulp has been stained and appears dark in the figures. As may be seen in FIG. 1 the prior art fabric comprises alternating rows of polyester fibers and wood pulp fibers and hence does not have a predominantly polymeric fiber face but a regular array of rows of polyester fibers 10 and wood pulp fibers 12. FIG. 2 discloses only rudimentary or discontinuous rows of polyester fibers 20 and wood pulp fibers 22. As may be seen, the wood pulp fibers are additionally scattered over the predominantly polyester surface. When viewed by the naked eye, the stained fabrics shown in FIGS. 1 and 2 have a different appearance with FIG. 1 displaying a striped configuration while FIG. 2 shows an overall mottled color.

Figure 3:
FIG. 3 is a 20× photomacrograph of a plan view of the polymeric fiber surface of a prior art fabric of FIG. 1 with polymer dissolved, displaying the wood pulp fibers only.
Figure 4:
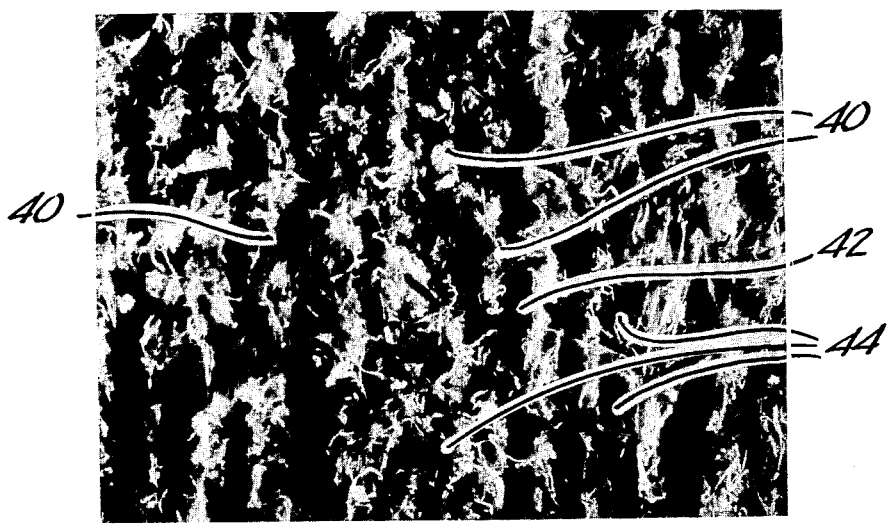
FIG. 4 is a 20× photomacrograph giving a plan view of the polymeric fiber surface of the fabric according to the present invention with the polymer dissolved, displaying the wood pulp fibers only.

In both FIGS. 3 and 4, the polymeric fibers have been dissolved out of the fabric leaving only the wood pulp fibers. FIG. 3 shows the polymeric fiber surface of the prior art fabric. The wood pulp fibers in FIG. 3 occur in entangled rows 30. Recesses 32 and 34 occur where the polymeric fibers have been dissolved away. In Applicants' fabric as shown in FIG. 4, the remaining wood pulp fibers occur in rudimentary, discontinuous entangled rows 40. The rudimentary or discontinuous rows of the polymeric fibers may be noted by the voids 42 where the polymeric fibers have been dissolved away. Regions 44 of the fabric show discontinuity of the wood pulp rows and the polymeric voids or rows and a general entangling of the wood pulp fibers.

Figure 5:
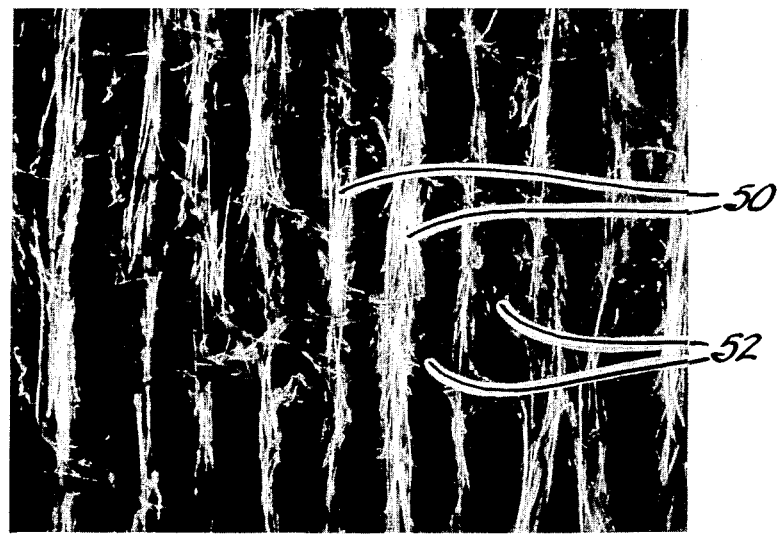
FIG. 5 is a 20× photomacrograph of FIG. 1 giving a plan view of the polymeric fiber surface of a prior art fabric with the wood pulp fibers dissolved, showing only the polymeric fibers.
Figure 6:
FIG. 6 is a 20× photomacrograph giving a plan view of the polymeric fiber surface of a fabric according to the present invention with the wood pulp fibers dissolved, showing only the polymeric fibers.

In FIGS. 5 and 6, the wood pulp fibers have been dissolved away leaving only the polymeric fibers. FIG. 5 shows the "polymeric fiber side" of the prior art fabric. As may be seen in FIG. 5 the polymeric fibers 50 are present in parallel rows of relatively unentangled fiber bundles 50 separated by voids 52 left by the dissolved wood pulp fibers. In Applicants' fabric shown in FIG. 6, the polymeric fibers show less bundling and more overall entanglement, however, rudimentary rows 60 of polymeric fibers may be seen. Voids 62 left by the wood pulp fibers occur between the rudimentary rows of the polymeric fibers and across the face of the fabric.

FIGS. 7 and 8 disclose the prior art fabric and Applicants' fabric respectively in cross-section. As may be seen in FIG. 7, the prior art fabric has a veneer of wood pulp on the surface 70 with the remainder of the fabric and the face 76 comprising alternating rows of polymeric fibers 72 and wood pulp fibers 74. Applicants' fabric shown in FIG. 8, has a predominantly wood pulp surface 80 and a predominantly polymeric fiber surface 82 with a very discontinuous pattern of groupings of wood pulp and polymeric fibers along the length of the fiber samples shown.

The fabric of the present invention displays enhanced machine direction, softness and drape as compared to the prior art fabric, as well as enhanced frictional properties. It may be surmised that the softness in the machine direction is achieved by the discontinuity of the rows of wood pulp and polymeric fibers. In addition it may be surmised that the slightly enhanced cross-directional strength of the fabric and the enhanced frictional properties of the fabric are due to the more overall entangled nature of the fabric of the present invention. The enhanced frictional properties of the fabric of the present invention are shown in Table 1.

TABLE 1

| Sample | Static Frictional Force (gms) | | Static Coefficient of Friction | |
|---|---|---|---|---|
| | Direction "A" | Direction "B" | Direction "A" | Direction "B" |
| Applicants' Roll #E92721-B-EF Fabric | 201 | 231 | 1.04 | 1.20 |
| Prior Art Fabric 450 TM | 112 | 173 | 0.57 | 0.90 |

As may be noted, Applicants' fabric in the "B" direction shows a 33 percent increase in both frictional force and coefficient of friction; while in the "A" direction discloses a 79 percent increase in static frictional force and a 82 percent increase in static coefficient of friction. The static frictional force and the static coefficient of friction were measured according to the standard ASTM Method D-1894-78, wherein "A" and "B" are arbitrarily assigned to the machine direction, and its reverse.

As may be seen in Table 2 below, samples 1, 2, 3, and 4 of the fabric of the present invention (made of entangled wood pulp and polyester fibers) show a decreased machine direction stiffness over the prior art Fabric 450 TM with an average decrease in the machine direction of 20 percent, and with a slightly enhanced cross-directional stiffness. The stiffness as set forth in Table 2 was measured according to the standard TAPPI T498 Handleometer test.

TABLE 2

| Stiffness (gms.) | Machine direction | Cross-direction |
|---|---|---|
| Sample 1 | 28.9 | 6.5 |
| 2 | 29.2 | 6.9 |
| 3 | 28.5 | 6.6 |
| 4 | 29.7 | 6.9 |
| Avg. | 29.1 | 6.7 |
| Fabric 450 TM | 36.6 | 5.3 |

The fabrics of the present invention are low cost disposable fabrics suitable for use in making repellant breathable drapes, wraps for medical components, or gowns for use in a sterile environment. The material is easily sterilizable and at least the cellulosic fibers may be subject to a repellant treatment. The polymeric fibers of the fabric of the present invention may comprise polyester, nylon, or polyolefin fibers having a length of from about one-half inch to about one and one-half inch, of 1 to 2 denier. The cellulosic fibers may comprise wood pulp or other cellulosic pulp fibers which may be repellant treated. The fabric is made utilizing the fluid entangling process similar to that set forth in the Evans U.S. Pat. No. 3,485,706. In making the fabric of the present invention, the polymeric fibers are laid down in a batt and partially entangled. The cellulosic fibers are then disposed atop the polymeric fibers and entangled into and through the polymeric fibers. In a preferred method, the cellulosic fibers are supplied and utilized in a repulpable, low wet strength tissue.

The foregoing description and drawings are illustrative but are not to be taken as limiting. Other variations and modifications are possible without departing from the spirit and scope of the present invention.

What is claimed is:

1. A sterile, low cost, disposable fabric suitable for use in making repellant, breathable, drapes or gowns with enhanced comfort for use in a sterile environment, said fabric comprising cellulosic fibers, and polymeric fibers of 1-2 denier, said fabric further comprising rudimentary discontinuous rows of entangled cellulosic fibers alternating with rudimentary discontinuous rows of loosely entangled polymer fibers, said rows extending in the machine direction, and said fabric having a surface comprising predominantly entangled cellulosic fibers and a surface comprising predominantly entangled polymeric fibers, at least said cellulosic fibers being subject to a repellant treatment, to yield a breathable, repellant soft fabric with enhanced drape and enhanced frictional properties.

2. A fabric as in claim 1 wherein said cellulosic fibers are present in a uniform distribution across the predominantly polymeric surface.

3. An operating room gown as in claim 1 wherein said fabric has a stiffness of less than about 50 gms. in the machine direction.

4. An operating room gown as in claim 1 wherein said cellulosic fibers comprise wood pulp fibers and said polymeric fibers comprise polyester fibers.

* * * * *